United States Patent [19]

Kricsfalussy et al.

[11] Patent Number: 5,599,965
[45] Date of Patent: *Feb. 4, 1997

[54] PROCESS FOR THE PREPARATION OF DIALKY CARBONATES

[75] Inventors: Zoltan Kricsfalussy; Helmut Waldmann; Hans-Joachim Traenckner, all of Leverkusen, Germany

[73] Assignee: Bayer Aktiengesellschaft, Leverkusen, Germany

[ * ] Notice: The term of this patent shall not extend beyond the expiration date of Pat. No. 5,523,452.

[21] Appl. No.: 279,328

[22] Filed: Jul. 22, 1994

[30] Foreign Application Priority Data

Jul. 30, 1993 [DE] Germany ............................ 43 25 651.1

[51] Int. Cl.$^6$ .................................................. C07C 69/96
[52] U.S. Cl. ............................................................. 558/277
[58] Field of Search ............................................... 558/277

[56] References Cited

U.S. PATENT DOCUMENTS

| | | | |
|---|---|---|---|
| Re. 29,338 | 8/1977 | Perrotti et al. | 558/277 |
| 5,142,087 | 8/1992 | Joerg et al. | 558/277 |
| 5,233,072 | 8/1993 | Kricsfalussy et al. | 558/277 |
| 5,274,163 | 12/1993 | Rechner et al. | 558/277 |

FOREIGN PATENT DOCUMENTS

| | | |
|---|---|---|
| 134668 | 3/1985 | European Pat. Off. . |
| 0534545 | 3/1993 | European Pat. Off. . |
| 0544162 | 6/1993 | European Pat. Off. . |
| 1574188 | 9/1980 | United Kingdom . |

OTHER PUBLICATIONS

Japanese Patents Report, 5:General Organic, p. 9, vol. $, No. 17; JA66–075394, JA–7011–129–R, Toyo Rayon Co., Ltd., "Organic carbonates from alcohol and carbon monoxide in the presence of cupric ions"; (Apr. 22, 1970).

*Primary Examiner*—Porfirio Nazario-Gonzalez
*Assistant Examiner*—Dwayne C. Jones
*Attorney, Agent, or Firm*—Sprung Horn Kramer & Woods

[57] ABSTRACT

$C_1$–$C_4$-Dialkyl carbonates can be obtained from the corresponding $C_1$–$C_4$-alkanols, carbon monoxide and oxygen by reacting these substances in the presence of Cu salts, the water of reaction being limited to less than 10 wt % in the reaction mixture by at least partial withdrawal.

11 Claims, 1 Drawing Sheet

PROCESS FOR THE PREPARATION OF DIALKY CARBONATES

BACKGROUND OF THE INVENTION

1. Field of the Invention

The invention relates to an improved process for the preparation of dialkyl carbonates by oxycarbonylating the corresponding alkanols in the presence of Cu salts, the water content being limited to less than 10 wt % of the reaction mixture.

Dialkyl carbonates, especially dimethyl carbonate, are intermediates of low toxicity and can replace toxic intermediates, such as phosgene or dimethyl sulphate, in many reactions. They are also non-corrosive. Their use does not give rise to environmentally harmful byproducts.

Examples of such reactions of dialkyl carbonates are the preparation of urethanes from aliphatic or aromatic amines, which can in turn be cleaved to give the corresponding isocyanates. As another example, dimethyl carbonate can replace dimethyl sulphate in the quaternization of amines or in the methylation of phenol or naphthols. Dimethyl carbonate can also be added to motor fuel, e.g. instead of lead compounds, to improve the octane number. Despite this importance of dialkyl carbonates, there is still no technically simple and environmentally acceptable production process which is suitable for large capacities without substantial byproduct formation or coupled material cycles.

2. Description of the Related Art

There are various processes, already technically proven on a small scale, for the preparation of dialkyl carbonates. The methods of preparation which are based on the catalytic reaction of alkanols with carbon monoxide and oxygen according to the equation below have been the subject of intensive study by a variety of working groups:

$$2 \text{ROH} + \text{CO} + 1/2 \text{O}_2 \xrightarrow{\text{copper salts}} \text{RO}-\text{CO}-\text{OR} + \text{H}_2\text{O}$$

In these reactions, the catalytically active copper compounds have been used in the form of various copper salts. When using copper(II) chloride as the catalyst according to JP-45/11129 (1970), unsatisfactory selectivities are obtained. Particularly troublesome is the formation of relatively large amounts of methyl chloride, which, because of its high volatility, tends to spread ubiquitously throughout the whole of the production plant and in practice can cause corrosion in the entire plant.

Better selectivities are obtained when using organic complexing agents (DE-A 21 10 194), but then there is the problem of separating off the catalyst salts, which are partly dissolved in the reaction mixture but are largely present as a suspension.

Carrying out this reaction according to DE-A 27 43 690 presents a very particular problem because the catalyst salts are practically completely undissolved in the reaction mixture and are only present as a suspension. These salts have to be conveyed through the reaction zone and the cooling units and separated off mechanically after the reaction, e.g. by means of centrifuges. In addition to the corrosion already mentioned, this also causes erosion, poor heat transfer, clogging and encrustation.

To avoid these disadvantages of a catalyst cycle, it has been proposed to keep the catalyst salts stationary in the reactor as a suspension and to meter methanol, CO and oxygen into the reactor, the dialkyl carbonate formed and the water of reaction being distilled out of the reactor together with the methanol used in excess (EP 0 413 215 A2). Here the liquid reaction medium consists essentially of the alkanol to be reacted (EP-0 413 215, page 3, line 52), so the molar ratio of alkanol to Cu salt is very high (preferably 1:0.01–0.05). This has the disadvantage of a relatively low reaction rate. A further problem here is the necessity to establish a low dialkyl carbonate concentration.

This is not easy since the reaction is carried out at a high system pressure and both dialkyl carbonate and water are very soluble in the reaction medium, which consists essentially of methanol. This means that a relatively large amount of inert gas or methanol gas has to be used to force the dialkyl carbonate and water to separate out.

Moreover, with this proposal, it must also be taken into account that the catalyst has to be changed after some time or continuously renewed in a certain proportion, which entails the problem, mentioned at the outset, of the separation, regeneration and recycling of the catalyst.

SUMMARY OF THE INVENTION

A process has been found for the preparation of dialkyl carbonates of the formula $$(\text{RO})_2\text{CO} \quad \quad (\text{I}),$$

wherein R is linear or branched $C_1$–$C_4$-alkyl, preferably methyl or ethyl and particularly preferably methyl, by reacting the corresponding alkanols of the formula $$\text{ROH} \quad \quad (\text{II}),$$

wherein R is as defined above, with carbon monoxide and oxygen in the presence of Cu salts, said process being characterized in that the reaction is carried out at 120° to 300° C., preferably at 120° to 180° C., and at 1 to 70 bar, preferably at 5 to 70 bar, in such a way that the water content is kept at a value of less than 10 wt % of the total reaction mixture by at least partial withdrawal of the water of reaction formed.

BRIEF DESCRIPTION OF THE DRAWING

The accompanying drawing shows an apparatus arrangement to carry out the inventive process, e.g. in a cascade of three reaction vessels A, B and C with the necessary equipment.

DETAILED DESCRIPTION OF THE INVENTION

Figure 1:
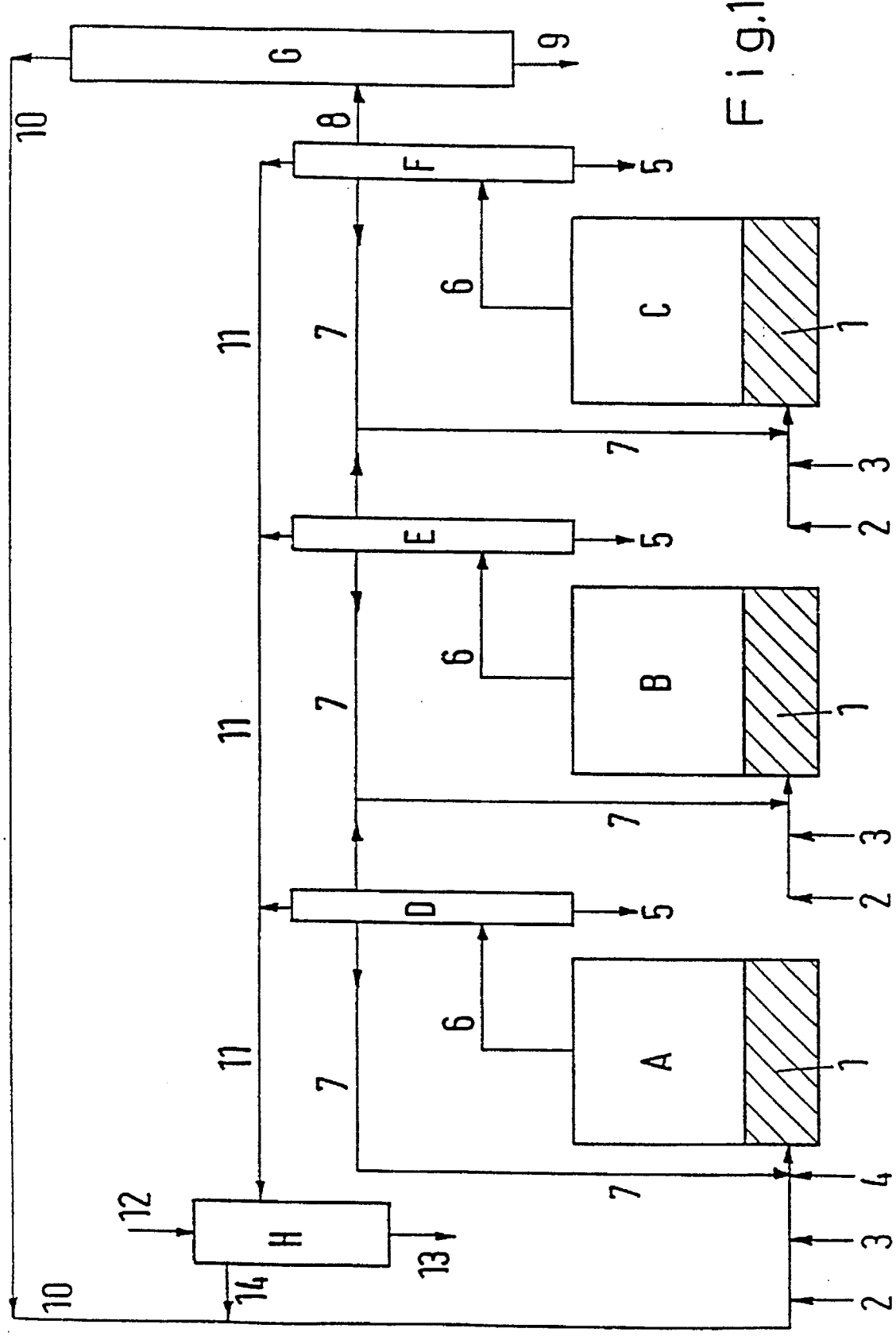

In this way the water content of the reaction mixture is controlled and reduced to low values. The reaction is generally carried out with a water content of less than 10 %, but it is advantageous to keep the water concentration below 6wt % in the reaction mixture. For a high conversion coupled with very high selectivities, it is particularly favourable to carry out the reaction with values of less than 3 wt %.

The process of the inventions preferably carried out using a salt melt containing a Cu salt, possible Cu salts being Cu(I) and Cu(II) compounds and mixtures thereof. In principle, all known Cu salts are suitable provided they are only soluble to some extent in the salt melt.

In addition to the halides, e.g. the chlorides or bromides, suitable salts are the cyanides, rhodanides, sulphates, nitrates, carbonates, acetates, formates, oxalates and alcoholates, e.g. Cu methoxychloride. Cu can also be used in the form of complex compounds such as the acetylacetonates, or Cu-N complexes such as Cupyridine or else Cu-dipyridyl complexes.

The salt melt is generally made up of mixtures of salts which have a low melting point, i.e. which form a eutectic. It is therefore advantageous to use the salts in the proportions which correspond to the composition of the eutectic. Such eutectics can be formed from different Cu salts or of Cu salts with other salts.

In addition to Cu salts, it is therefore possible in principle to use any chemically inert salts or else salts which are catalytically active in terms of the invention, i.e. which lower the activation energy for the oxycarbonylation of alkanols. A large number of salts or salt-like compounds can be used here in addition to Cu salts. It is normal to use mixtures of Cu salts and such salt-like compounds. It is preferable to use the halides of the main groups and subgroups 1 to 3. Alkali metal chlorides, such as NaCl or KCl, or alkaline earth metal chlorides, such as $CaCl_2$ or $MgCl_2$, and also $ZnCl_2$, are particularly suitable. It is also possible, however, to use less common compounds such as thallium, indium or gallium chlorides.

A very suitable melt consists for example of Cu (I) chloride and KCl in varying proportions. It is usual to choose mixtures with a high content of Cu compounds, e.g. a weight ratio of Cu(I) chloride to KCl of 60 to 75 to 40 to 25.

The reaction temperature is generally about 120° C. to 300° C., preferably 120° C. to 180° C., typical reaction temperatures being 120° C. to 150° C.

The reaction can be carried out at normal pressure. To attain a sufficiently high reaction rate, however, it is convenient to operate at elevated pressure, e.g. at 5 to 70 bar, preferably at 10 to 50 bar and particularly preferably at 25 to 50 bar.

The molar ratios of the reactants used are important in terms of the reaction rate and the selectivity of the reaction. Examples of by-products which are formed if these conditions are not observed are formaldehyde dimethylacetal or methyl chloride, the latter being particularly troublesome. It is usual to choose a molar excess of methanol to carbon monoxide and also an excess of carbon monoxide to oxygen, but at most molar amounts of CO or $O_2$. Thus the chosen molar ratios of alkanol to CO and $O_2$ are 1:1–0.01:1–0.01, preferably 1:0.5–0.02:0.3–0.02. This results in a methanol conversion of 10 to 50%, for example, and a CO conversion of 10 to 80%. Oxygen is generally fully converted. It is of course necessary to respect the explosion limits when proportioning the amounts. The reaction can optionally be carried out in the presence of inert gases such as $N_2$ or $CO_2$.

The oxygen can be used for example in the form of atmospheric air or $O_2$-enriched air.

The unreacted methanol and CO can be recycled after separation of the dialkyl carbonate and $H_2O$ and optionally also $CO_2$.

The water can be withdrawn using any known procedures of process technology. For example, in one possible procedure, after the reaction has advanced to a certain point, e.g. at an alkanol conversion of 8 to 35%, preferably 10 to 27% and particularly preferably 15 to 25%, the organic components of the reaction mixture are separated off in a manner known per se and the water of reaction is separated off afterwards or at the same time, e.g. by distillation. In the case of the preparation of dimethyl carbonate, for example, this distillation is carried out in such a way that a reaction mixture composed of 20 to 25% of dimethyl carbonate, 4 to 6% of water and the remainder methanol is fed into the middle of a fractionation column containing ca. 25 theoretical plates, and water is withdrawn as the bottom product at approximately atmospheric pressure, mixtures of 20 to 27% of dimethyl carbonate and the remainder methanol being obtained as the top product. This top product can be re-used in the reaction with carbon monoxide and an oxygen-containing gas.

In this renewed conversion of the reaction mixture, the reaction can be pursued for example to a water content of 4 to 6% to give reaction mixtures with a dialkyl carbonate content of 50 to 55 wt % in the case of very high selectivities. By renewed and optionally repeated withdrawal of the water, it is possible to attain a dialkyl carbonate content of about 75%.

The particular advantage of the process according to the invention is that it gives reaction mixtures with high dialkyl carbonate contents, for example 50 to 70 wt %, from which the pure dialkyl carbonate can be isolated in a particularly simple and economic manner.

Alternative possible methods of process technology for removing the water of reaction are other dewatering processes, e.g. azeotropic distillation, optionally with the addition of an azeotropic agent to the reaction mixture. Extraction methods can also advantageously be used. A further possibility, however, is to bind the water of reaction chemically or adsorptively, although removal by distillation is preferred.

The process according to the invention can be carried out in the various known types of reactor, for example in a stirred tank with a gas-dispersing stirrer. The operation can be carried out batchwise or else continuously. For continuous operation, reaction tank cascades comprising 3 to 5 reactors, for example, are also suitable. However, a one-stage or multistage bubble column is also suitable for the process.

The gas load can be varied within wide limits according to pressure and temperature, so that space-time yields of between 10 and 200 g/l.h can be achieved.

The heat of reaction can be removed by means of cooling units. In one particular embodiment, however, the process is carried out in a so-called boiling reactor, from which the heat of reaction is dissipated through evaporation of the product. Thus, for example, in the case of a liquid alkanol feed, the heat of reaction is dissipated through evaporation of the alkanol without the need for cooling units on the reactor. The reaction products, namely dialkyl carbonate and water, are discharged from the reactor through the gas stream. The concentration of the substances in the gas stream depends on the pressure and temperature. It can therefore be advantageous, especially at elevated pressure, briefly to relieve the pressure and finally to operate under pressure again (so-called pressure swing technique). Thus, for example, in the preparation of dimethyl carbonate, one possible procedure is to operate for 1 min. to 10 min. at elevated pressure, for example at 25 to 50 bar, and then to reduce the system pressure to about 10 to 0.8 bar, preferably 3 to 1 bar. The melt remains completely in the reaction zone and the organic substances, e.g. dimethyl carbonate and methanol, distil almost completely out of the reactor. This phased changing of the system pressure, which facilitates the separation of the reaction products, is particularly suitable for the process according to the invention.

Examples of suitable materials for the reactors are corrosion-resistant special steels, enamelled steel, glass, or special metals such as tantalum.

The process according to the invention can also be carried out industrially on a larger scale. As shown in FIG. 1, for example, a product stream containing 55 to 57 wt % of dialkyl carbonate can be obtained in a multistage, e.g. 3-stage, reaction cascade, a distillation column for water removal being attached to each reactor unit.

The following equipment is illustrated in FIG. 1: Three reactors A, B and C; three corresponding distillation columns D, E and F for withdrawing water; a distillation column G for recovering dialkyl carbonate; and a gas scrubber H for scrubbing out $CO_2$ (formed as an undesirable by-product by the oxidation of CO). The following reactants are also shown in FIG. 1: Melt (1) containing Cu salt in A, B and C; CO feed (2) or $O_2$ feed (3); alkanol feed (4); withdrawn $H_2O$ (5); removed organic reaction mixture (6); alkyl carbonate/alkanol mixture (7) for recycling; alkyl carbonate/alkanol mixture (8) for recovering alkyl carbonate; concentrated alkyl carbonate (9); alkanol (10) for recycling, optionally mixed with alkyl carbonate; $CO/CO_2$ mixture (11) flowing out of D, E and F, which can optionally contain residual $O_2$; sodium hydroxide feed (12) for the gas scrubber; $NaHCO_3$ discharge (13); and CO (14) for recycling, optionally together with residual $O_2$. For the sake of simplicity, no reference has been made to inert gas.

EXAMPLE 1

94 ml of a salt mixture of 72 wt % of Cu(I) chloride and 28 wt % of KCl, melted at 150° C., were placed in a steel vessel provided with a Ta insert and equipped with a feed tube, a temperature-measuring device and a pressure-maintaining device. 390 g/h of methanol, 36 l/h of CO and 42 l/h of air were metered in at 150° C. and 50 bar. After the pressure had been relieved, the reaction mixture was metered into the reactor again without being worked up.

After recycling three times, the methanol conversion was 27% and the dimethyl carbonate selectivity was 98%.

EXAMPLE 2

The reaction mixture of Example 1, obtained after recycling three times, was dewatered in a distillation column and metered into the reactor under the conditions described in Example 1.

After recycling three times, the methanol conversion was 55% and the dimethyl carbonate selectivity was 97%.

EXAMPLE 3

A mixture of 50% of methanol and 50% of dimethyl carbonate was metered into the reactor under the conditions described in Example 1. After one pass, the methanol conversion was 56% and the dimethyl carbonate selectivity was 98%.

EXAMPLE 4

A mixture of 40% of methanol and 60% of dimethyl carbonate was metered into the reactor under the conditions described in Example 1. After one pass, the methanol conversion was 65% and the dimethyl carbonate selectivity was 98%.

EXAMPLE 5

A mixture of 30% of methanol and 70% of dimethyl carbonate was metered into the reactor under the conditions described in Example 1. After one pass, the methanol conversion was 73% and the dimethyl carbonate selectivity was 98%.

What is claimed is:

1. A process for the preparation of a dialkyl carbonate of the formula $$(RO)_2CO,$$

wherein R is linear or branched $C_1$–$C_4$-alkyl, by reacting the corresponding alkanol of the formula ROH, wherein R is as defined above, with carbon monoxide and oxygen in the presence of a salt melt containing a Cu salt wherein a molar ratio of alkanol: $CO:O_2$=1:1-0.01:1-0.01 is established and the reaction is carried out at 120° to 300° C. and at 25 to 50 bar, and the pressure is relieved in stages to 10 to 0.8 bar in order to distill water and organic components out of the reaction medium, the salt melt remaining in the reaction medium, and the pressure is then allowed to increase to 25 to 50 bar again whereby the water content is kept at a value of less than 10 wt % of the total reaction mixture and the resulting distillate is fed into a fractionation column, water is obtained as the bottom product and withdrawn, and dialkyl carbonate and alkanol as the top product are recycled into the reaction.

2. The process of claim 1, wherein R is methyl or ethyl.

3. The process of claim 2, wherein R is methyl.

4. The process of claim 1, which is carried out at 120° to 180° C.

5. The process of claim 1, wherein the water content is kept at a value of less than 6 wt %.

6. The process of claim 5, wherein the water content is kept at a value of less than 3 wt %.

7. The process of claim 1, wherein a melt of Cu(I) chloride and KCl is used.

8. The process of claim 7, wherein a weight ratio of CuCl:KCl =60 to 75:40 to 25 is established.

9. The process of claim 1, wherein a molar ratio of alkanol: $CO:O_2$ =1:0.5-0.02:0.3-0.02, is established.

10. The process of claim 1, which is carried out continuously in a stirred tank cascade comprising 3 to 5 reactors.

11. The process of claim 1, wherein the pressure is relieved in stages to 3 to 1 bar.

* * * * *